United States Patent [19]
Balkovec et al.

[11] Patent Number: 5,854,212
[45] Date of Patent: Dec. 29, 1998

[54] CYCLOHEXAPEPTIDYL BISAMINE COMPOUND, COMPOSITIONS CONTAINING SAID COMPOUND AND METHODS OF USE

[75] Inventors: James M. Balkovec, North Plainfield; Frances A. Bouffard, Scotch Plains; James F. Dropinski, Piscataway, all of N.J.

[73] Assignee: Merck & Co., Inc., Rahway, N.J.

[21] Appl. No.: 738,489

[22] Filed: Oct. 23, 1996

[51] Int. Cl.$^6$ .............................. A61K 38/12; C07K 7/64
[52] U.S. Cl. .................... 514/11; 514/9; 514/2; 514/16; 514/17; 530/317; 530/329
[58] Field of Search ..................... 530/317, 329; 514/9, 11, 16, 17

[56] References Cited

U.S. PATENT DOCUMENTS

| | | | |
|---|---|---|---|
| 5,166,135 | 11/1992 | Schmatz | 514/11 |
| 5,378,804 | 1/1995 | Balkovec et al. | 514/11 |
| 5,516,757 | 5/1996 | Balkovec | 514/11 |

FOREIGN PATENT DOCUMENTS

| | | |
|---|---|---|
| 0 535 967 A2 | 4/1993 | European Pat. Off. |
| 0 644 199 A1 | 3/1995 | European Pat. Off. |
| WO 94/21677 | 3/1994 | WIPO |
| 9409033 | 4/1994 | WIPO |
| 9608267 | 3/1996 | WIPO |

*Primary Examiner*—Cecilia J. Tsang
*Assistant Examiner*—S. G. Marshall
*Attorney, Agent, or Firm*—Elliott Korsen; Mark R. Daniel

[57] ABSTRACT

A compound of the formula

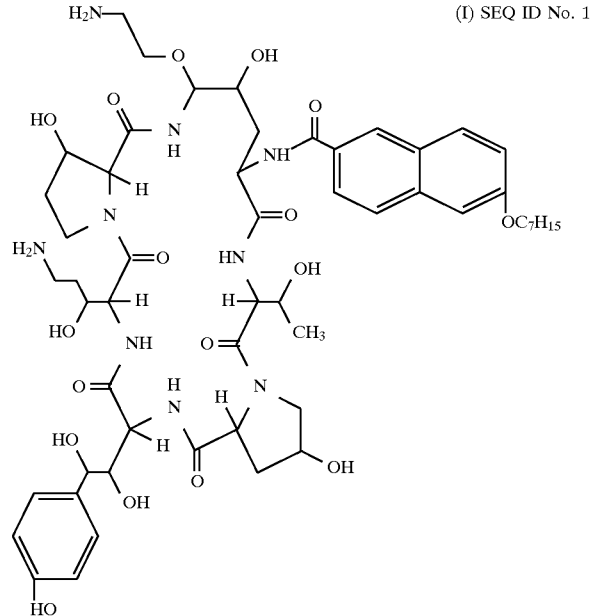

is disclosed which is useful for the treatment of fungal infections and for the treatment of infections caused by *Pneumocystis carinii*.

18 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:1:

Xaa  Thr  Xaa  Xaa  Xaa  Xaa
1                      5

CYCLOHEXAPEPTIDYL BISAMINE COMPOUND, COMPOSITIONS CONTAINING SAID COMPOUND AND METHODS OF USE

BACKGROUND OF THE INVENTION

The present invention relates to an antifungal and antipneumocystis agent of the pneumocandin class, in which the aryl side chain on the 5-aminoethyloxy-4-hydroxyornithine subunit of the hexapeptide consists of a naphthoyl group with an $OC_7H_{15}$ substituent.

Pending U.S. patent application Ser. No. 07/936,558 filed Sep. 3, 1992 generally discloses pneumocandins containing an aminoethyl ether it the C-5 ornithine position as well as an amine group at the 5th position of the hexapeptide, as having antifungal activity. EP Publication No. 0 535 967 published Apr. 7, 1993 also discloses these pneumocandins.

The compound of the present invention is characterized by an antibiotic spectrum which is largely focused on Candida, Aspergillus, and *Pneumocystis carinii*. Also, the present compound has safety, and pharmacokinetic properties which are superior to other compounds in the class.

There is an increasing need for agents which are effective against opportunistic mycotic infections by such agents as Candida, Aspergillus, Cryptococcus and *Pneumocystis carinii*. The present treatments, i.e., amphotericin B and fluconazole, cause severe side effects or are only fungistatic. The compound of the present invention is considered to be both safe and fungicidal.

SUMMARY OF THE INVENTION

The present invention relates to a novel cyclohexapeptidyl bisamine compound of the formula:

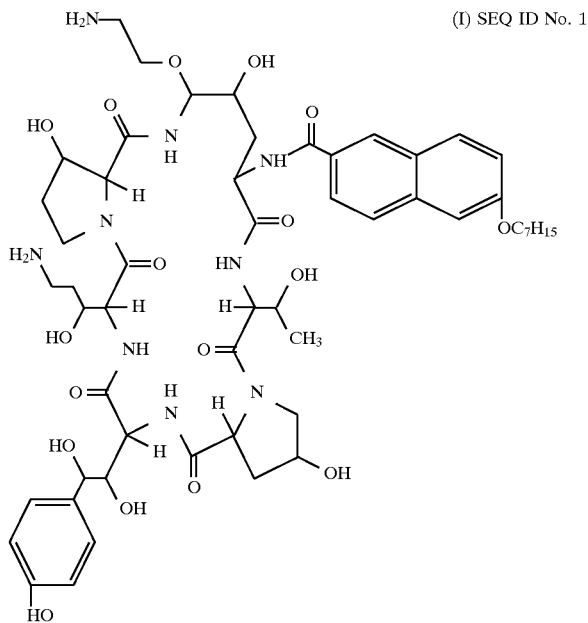

(I) SEQ ID No. 1 or its acid addition salt.

The present invention also relates to a pharmaceutical composition comprised of the compound in combination with a pharmaceutically acceptable carrier.

Additionally, the present invention relates to a method for treating fungal infections, in particular those caused by Candida, Aspergillus and *Pneumocystis carinii* which comprises administering the compound of formula I to a patient in need of such treatment in an amount effective to treat the fungal infection. The invention additionally relates to a method for preventing *Pneumocystis carinii* infections in a patient which comprises administration of a preventative amount of the compound of formula I.

Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic, pamoic and the like, and include other acids related to the pharmaceutically acceptable salts listed in Journal of Pharmaceutical Science, 66, 2 (1977).

When the compound is a free amine, it is soluble in lower alcohols and polar aprotic solvents such as dimethylformamide (DMF) and pyridine. It is insoluble in solvents such as ether and acetonitrile. When the compound is a quaternary ammonium salt or protonated amine, it is soluble in water and polar solvents.

The compound of the present invention is useful as an antibiotic, especially as an antifungal agent or as an anti-protozoal agent. As an antifungal agent, it is useful for the control of both filamentous fungi and yeast. It is especially adaptable to be employed for the treatment of mycotic infections in mammals, especially those caused by Candida species such as *C. albicans, C. tropicalis, C. krusei, C. glabrata* and *C. pseudotropicalis,* and Aspergillus species such as *A. fumigatus, A. flavus* and *A. niger.* It is also useful for the treatment and/or prevention of *Pneumocystis carinii* pneumonia to which immune compromised patients are especially susceptible as hereinafter described.

The previously noted solubility properties are advantageous for utilization in therapeutic applications, especially in injectible compositions.

The compound of the present invention may be obtained from natural products or derivatives of natural products through a sequence of reactions seen in the accompanying reaction schemes or from one of the intermediates which are claimed in concurrently filed copending applications.

The compound of the present invention may be prepared by two different methods. In the first method, illustrated in Scheme 1, the starting material which is represented by formula (E), is a natural product disclosed in U.S. Pat. No. 5,202,309 issued Apr. 13, 1993. The 3-hydroxyglutamine residue may be reduced to a 3-hydroxyornithine residue (Compound F) using any suitable reducing agent. However, preferred agents include a borane complex such as borane with tetrahydrofuran or dimethylsulfide or $BH_2Cl$ with dimethylsulfide or a metal boride such as $ZrCl_4/NaBH_4$. Compound F has been described in copending application Ser. No. 07/936,561 filed Sep. 3, 1992. Etherification at the 5-position of the 4,5-dihydroxyornithine residue of Compound F may be carried out with ethanolamine and a suitable acid catalyst to give bis-amine Compound G. Compound G has been described in copending application Ser. No. 07/936,558 filed Sep. 3, 1992. The dimethylmyristoyl side chain of Compound G may be deacylated enzymatically with *Comamonas acidovorans* to give triamine Compound H. Compound H is the subject of copending application Ser. No. 08/295,176 filed Aug. 23, 1994. Other suitable enzymatic preparations from a variety of organisms may also be employed for the deacylation. Selective protection of two of the three amine groups of Compound H may be accomplished by any number of reagents. Benzyl 4-nitrophenylcarbonate illustrates this protection step to give Compound J and is shown in Scheme 1. Treatment of Compound J with an activated acylating form of 6-n-heptyloxy-2-naphthoic acid gives the reacylated cyclopeptide K. The preferred activated form is the pentafluorophenyl naphthoate ester. The protecting groups are removed by a suitable method, that being hydrogenolysis for CBz, to give the compound of the present invention.

SCHEME 1
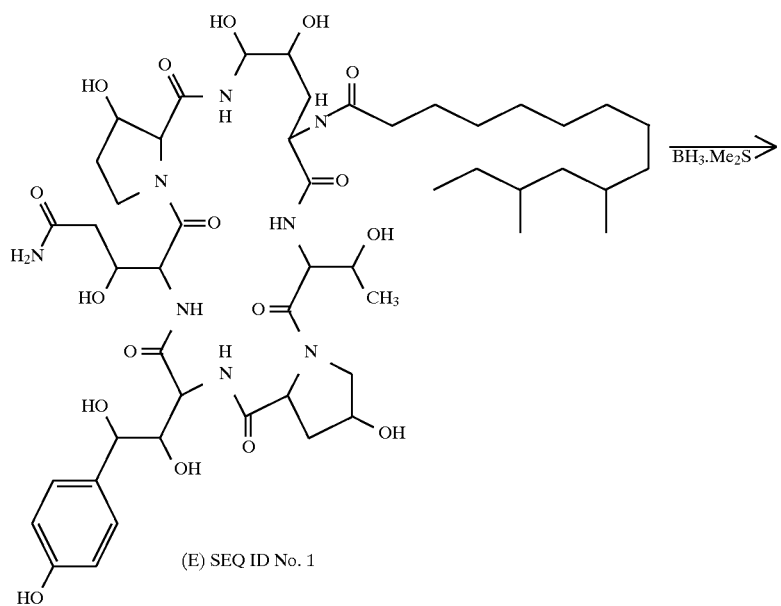
(E) SEQ ID No. 1
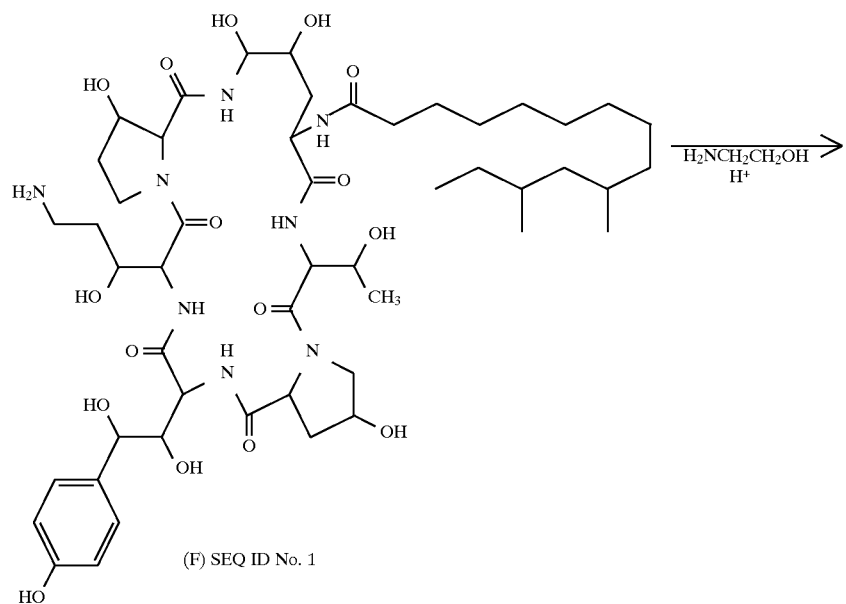
(F) SEQ ID No. 1

-continued
SCHEME 1
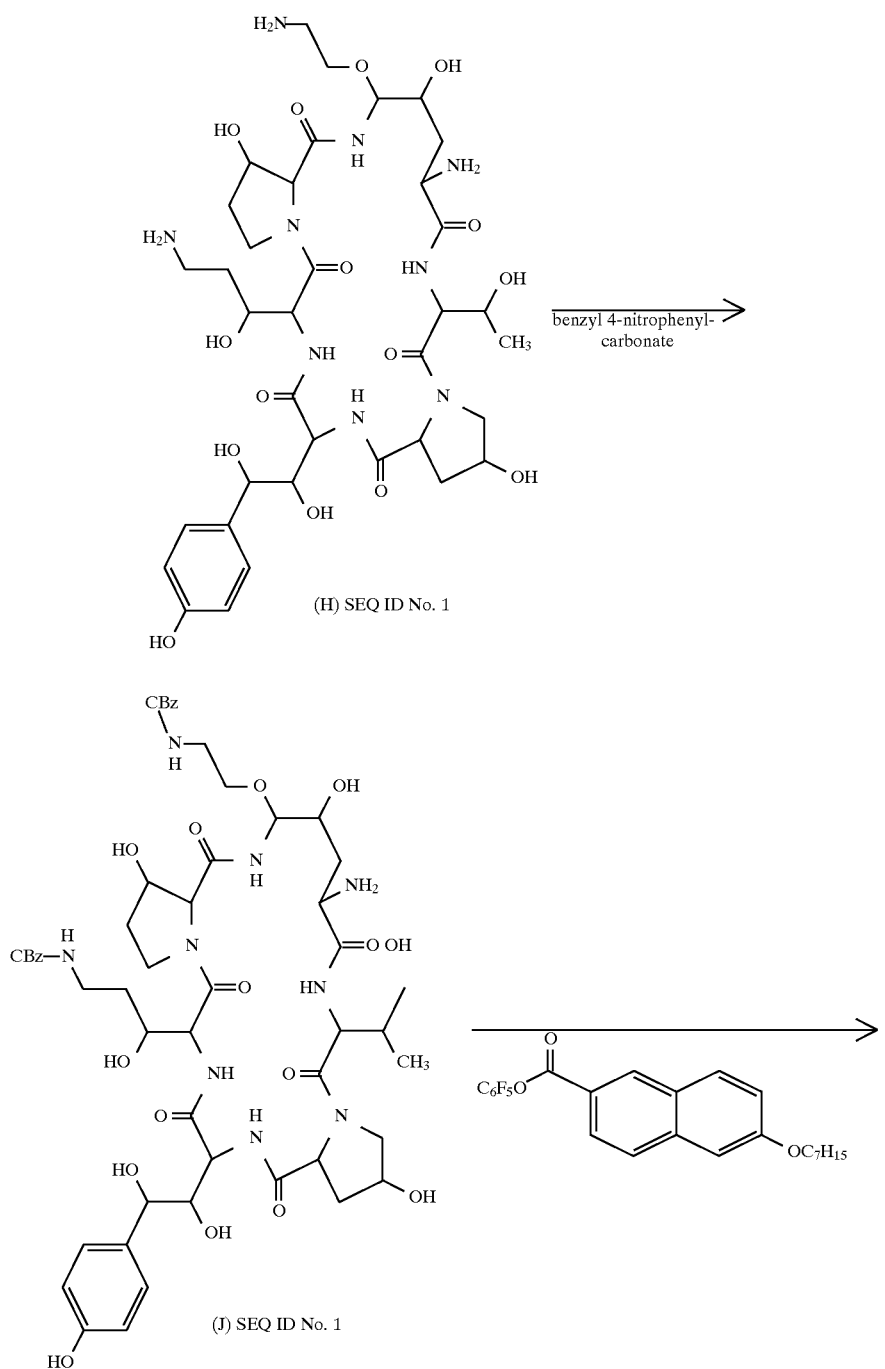
(H) SEQ ID No. 1
(J) SEQ ID No. 1

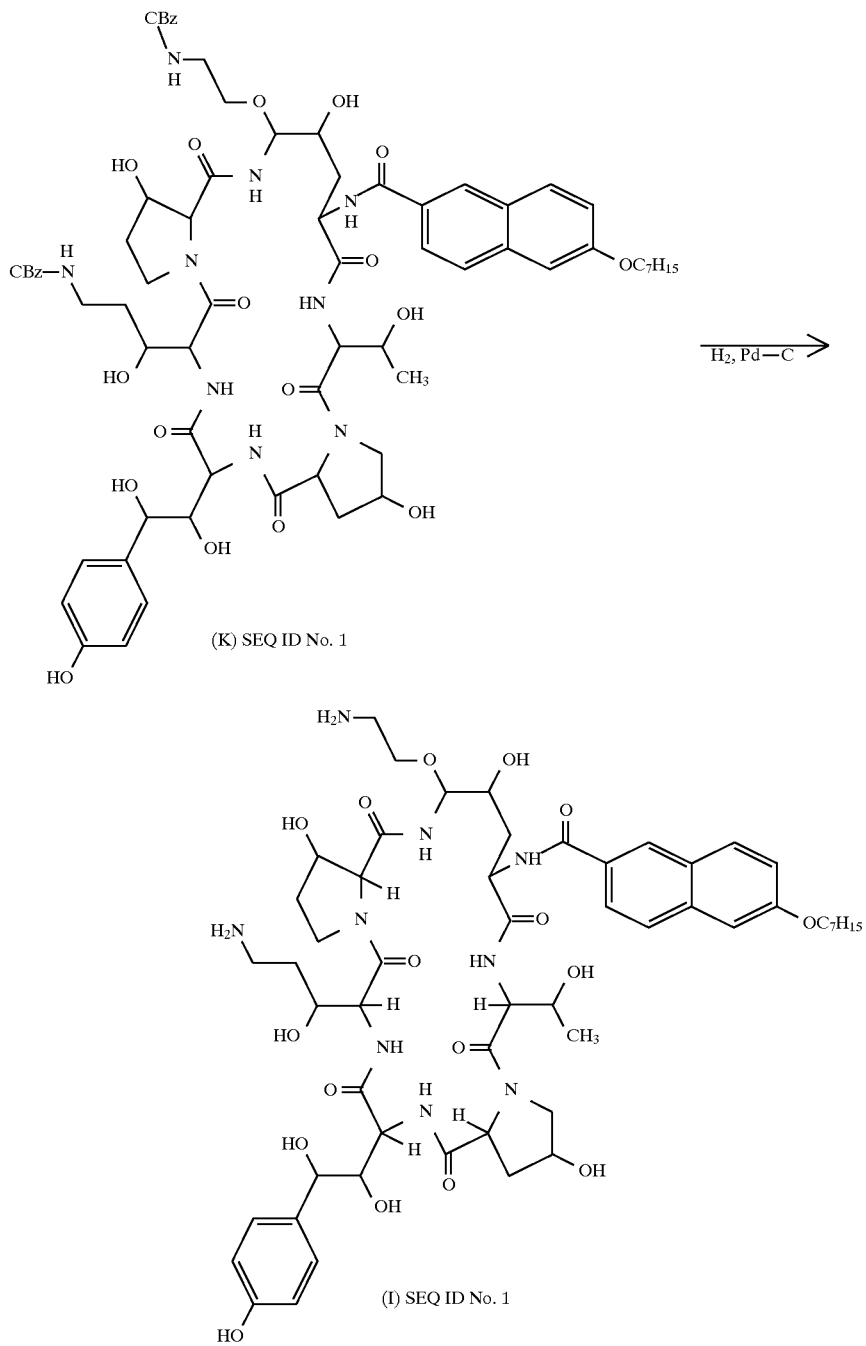

Alternatively, as shown in Scheme 2, the compound of the present invention may be obtained by subjecting Compound E to enzymatic reaction with a preparation of *Comamonas acidovorans* or any suitable organism to give the deacylated cyclopeptide Compound L. Compound L is the subject of U.S. Pat. No. 5,310,873 issued May 10, 1994. Acylation of the free amine group of Compound L may be accomplished using an activated acylating form of 6-n-heptyloxy-2-naphthoic acid. The pentafluorophenyl ester of 6-n-heptyloxy-2-naphthoic acid illustrates the transformation of Compound L to Compound M and is preferred. Reduction of Compound M with a suitable reducing agent such as borane-dimethyl sulfide complex affords amine Compound N. Etherification of Compound N with ethanolamine employing an acid catalyst affords the Compound of the present invention.

SCHEME 2
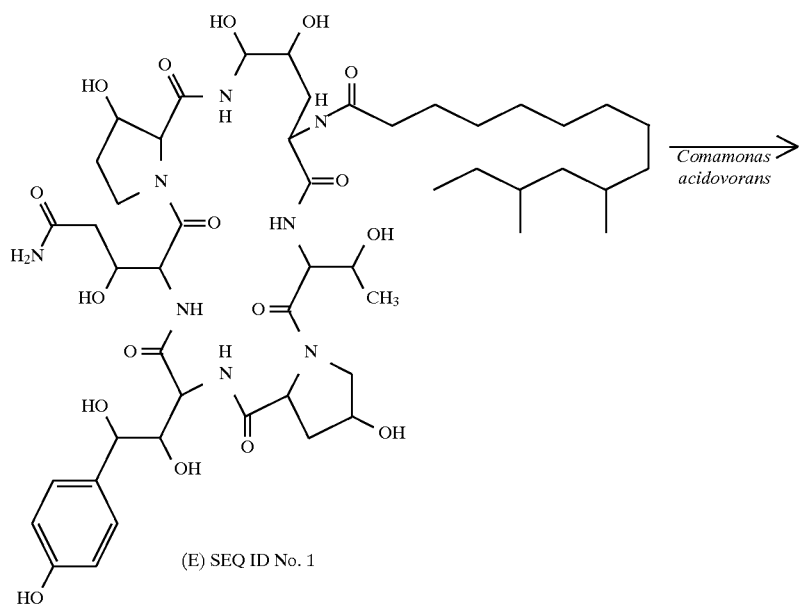
(E) SEQ ID No. 1
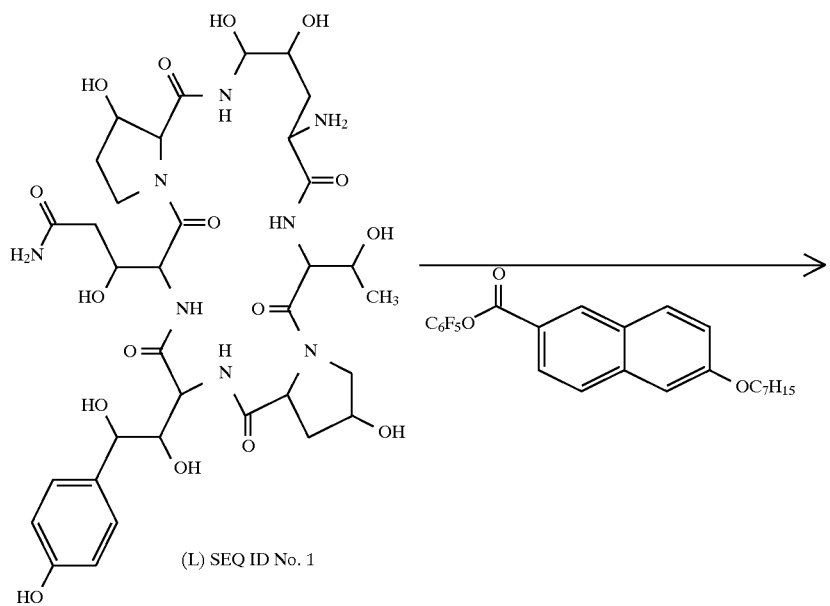
(L) SEQ ID No. 1

-continued
SCHEME 2
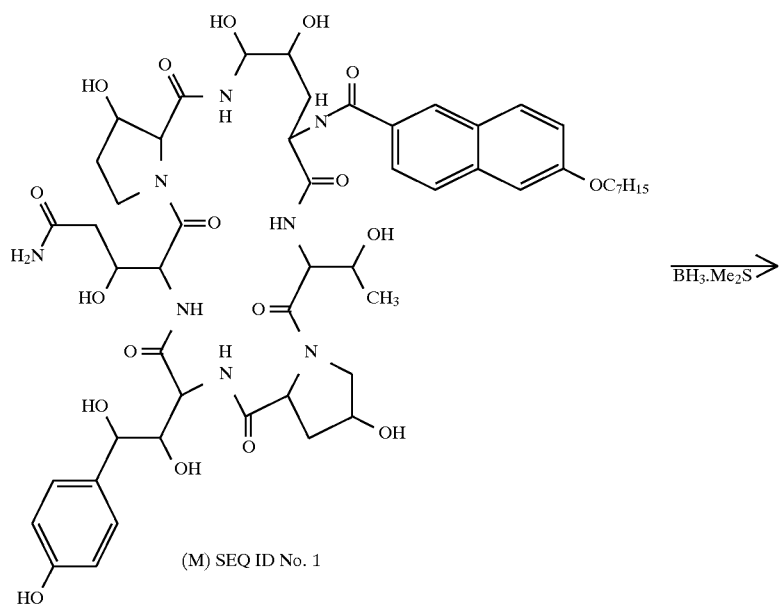
(M) SEQ ID No. 1
$\xrightarrow{BH_3 \cdot Me_2S}$
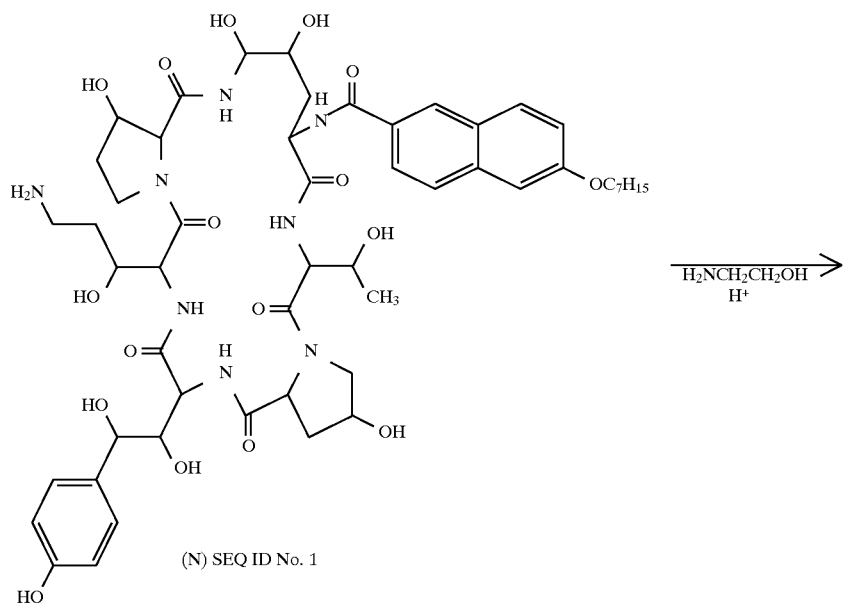
(N) SEQ ID No. 1
$\xrightarrow[H^+]{H_2NCH_2CH_2OH}$ -continued
SCHEME 2

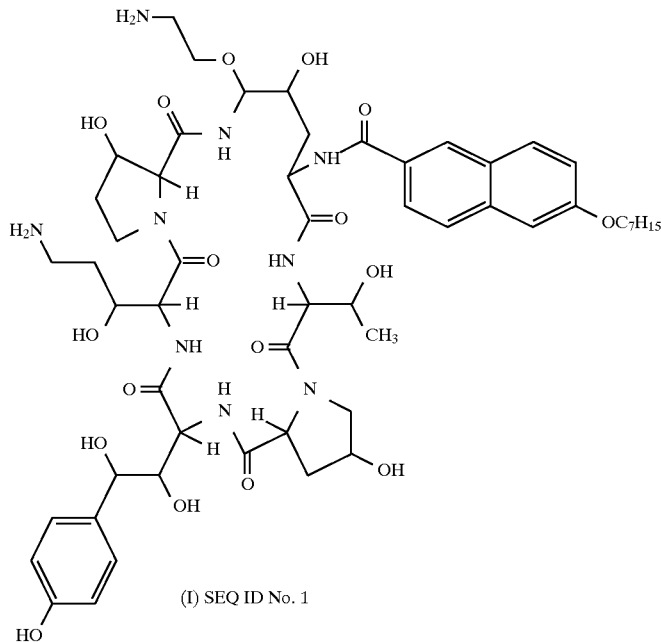

(I) SEQ ID No. 1

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1 percent dextrose (YNBD).

In a representative assay, Compound I was solubilized in 100 percent dimethyl sulfoxide (DMSO) at an initial concentration of 5 mg/ml. Once dissolved, the drug stock was brought to a concentration of 512 µg/ml by dilution in water such that the final DMSO concentration was about 10 percent. The solution was then dispensed via a multichannel pipetter into the first column of a 96-well plate (each well containing 0.075 ml of YNBD), resulting in a drug concentration of 256 µg/ml. Compounds in the first column were diluted 2-fold across the rows yielding final drug concentrations ranging from 256 µg/ml to 0.12 µg/ml.

Four-hour broth cultures of organisms to be tested were adjusted using a spectrophotometer at 600 nm to equal a 0.5 McFarland Standard. This suspension was diluted 1:100 in YNBD to yield a cell concentration of $1-5 \times 10^4$ colony forming units (CFU)/ml. Aliquots of the suspension (0.075 ml) were inoculated into each well of the microtiter plate resulting in a final cell inoculum of $5-25 \times 10^3$. CFU/ml and final drug concentrations ranging from 128 µg/ml to 0.06 µg/ml. Each assay includes one row for drug-free control wells and one row for cell-free control wells.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. However, for *Cryptoccoccus neoformans* strains, SDA plates were inoculated at 48 hours and incubated 48 hours after being spotted on SDA before making minimum fungicidal concentration (MFC) readings.

The results were as follows:

| Organism | | MFC µg/mL |
|---|---|---|
| C. albicans | CLY 539 | <0.06 |
| C. albicans | MY 1055 | <0.06 |
| C. glabrata | MY 1381 | <0.06 |
| C. guillermondii | MY 1019 | 0.25 |
| C. krusei | | <0.06 |
| C. parapsilosis | MY 1010 | <0.06 |
| C. pseudotropicalis | MY 2099 | <0.06 |
| C. tropicalis | MY 1012 | <0.06 |
| Cr. neoformans | MY 2061 | 128 |
| Cr. neoformans | MY 2062 | 32 |

Compound I also shows in vivo effectiveness against fungi.

Growth from an overnight SDA culture of *Candida albicans* MY 1055 was suspended in sterile saline and the cell concentration determined by hemacytometer count and the cell suspension adjusted to $3.75 \times 10^5$ cells/ml. Then 0.2 milliliter of this suspension was administered I.V. in the tail vein of mice so that the final inoculum was $7.5 \times 10^4$ cells/mouse.

The assay then was carried out by administering aqueous solutions of Compound I at various concentrations intraperitoneally (I.P.), twice daily (b.i.d.) for two consecutive days to 18 to 20 gram female DBA/2 mice, which previously had been infected with *Candida albicans* in the manner described above. Distilled water was administered I.P. to C. *albicans* challenged mice as controls. After four days, the mice were sacrificed by carbon dioxide gas, paired kidneys were removed aseptically and placed in sterile polyethylene bags containing 5 milliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram of kidneys. Compound I showed greater than 99 percent reduction of recoverable Candida CFUs when dosed at 0.375 and 0.09 mg/kg I.P. as described above.

The compound of the present invention may also be useful for inhibiting or alleviating *Pneumocystis carinii* infections in immune compromised patients. The efficacy of the compound of the present invention for therapeutic or anti-infective purposes may be demonstrated in studies on inmmunosuppressed mice.

In a representative study, the effectiveness of Compound I was determined. Mice (weighing approximately 20 grams) were immunosuppressed with dexamethasone in the drinking water (2.0 mg/L) and maintained on a low protein diet for seven weeks to induce the development of Pneumocystis pneumonia from a latent infection. Before drug treatment, two mice were sacrificed to confirm the presence of *Pneumocystis carinii* pneumonia (PCP); both mice were found to have infections. Five mice (weighing approximately 20 grams) were injected twice daily for four days subcutaneously (sc) with the compound in 0.25 ml of vehicle (distilled water). A vehicle control was also carried out. All animals continued to receive dexamethasone in the drinking water and low protein diet during the treatment period. At the completion of the treatment, all animals were sacrificed, the lungs were removed and processed, and the extent of disease determined by microscopic analysis of stained slides. The results of this study showed Compound I was >95 percent effective in reducing *P. carinii* cysts in 5 mice when dosed at 0.125 mg/kg.

The compound of the present invention has surprising and unexpected safety benefits in that there is markedly improved acute tolerability in mammals than with other related compounds. To demonstrate, laboratory test animals (rhesus monkeys) were dosed with the compound intravenously and observed for any abnormal effects. Unexpectedly, no notable response was observed for the compound of the present invention when dosed at identical levels of related compounds that do cause cardiovascular effects.

Additionally, the acute tolerability of the compound of the present invention in mice has been shown to be superior to that of related compounds.

The outstanding properties are most effectively utilized when compound I is formulated into novel pharmaceutical compositions with a pharmaceutically acceptable carrier according to conventional pharmaceutical compounding techniques.

The novel compositions contain at least a therapeutic antifungal or antipneumocystis amount of the active compound of the present invention. Generally, the composition contains at least 1 percent by weight of Compound I. Concentrate compositions suitable for dilutions prior to use may contain 90 percent or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with a lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injection take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. Compound I may also be solubilized in alcohol/propylene glycol or polyethylene glycol for drip intravenous administration. These compositions also may be presented in unit dosage form in ampoules or in multidose containers, preferably with added preservative. Alteratively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 10 to 500 milligrams of the compound.

When the compound of the present invention is for antifungal use, any method of administration may be employed.

When Compound I is to be employed for control of pneumocystis infections any method may be employed although it may be desirable to directly treat lung and bronchi. In such administration inhalation methods are employed. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of the compound in suitable propellants, such as fluorocarbons or hydrocarbons.

Although the compound of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The invention is further described in connection with the following non-limiting examples.

EXAMPLE 1

Part A. Preparation of Compound F

Compound E (15.9 g, 89 area % pure, 3.4 wt % water, 0.0128 mol) was added to dry THF (0.64 L) and the suspension was dried to <10 mol % water by refluxing through a bed of 3 Å molecular sieves. Additional dry THF was added to reconstitute the mixture to the original volume and the suspension was cooled to <4° C. with an ice/water/methanol bath.

Neat $BH_3 \cdot SMe_2$ (10.91 g, 0.144 mol) was added over ten minutes and the reaction mixture was maintained at 0°–4° C. The reaction progress was monitored by HPLC until the ratio of starting material to product was 1:1 indicating the end of the reaction (3.5 h). At 4 hours, the mixture was cooled to −12° C. and slowly quenched with 2N HCl (0.036 L). This solution was diluted to 1.14 L with water. The assay yield of Compound F was 6.60 g (47%).

The quenched solution was diluted to 4 L and loaded onto a medium-pressure column of LiChroprep RP-C18 adsorbent (158 g). After loading, the column was washed with 1.2 L water and the amine was eluted with 1.9 L of 1:4 v/v acetonitrile/water, and then 0.38 L of 1:3 v/v acetonitrile/water.

The rich cuts (>80 area %) were combined and diluted with water to a 1:7.3 v/v acetonitrile/water solution (1.70 L total). This mixture was loaded to the same column described above, and the column was washed with 0.57 L water. The desired compound was eluted with 0.57 L methanol. The rich cut fractions (>85 area %) were combined and concentrated by rotary evaporation and static high vacuum to give 6.81 g (87 wt % pure, 6.8 wt % water) containing 5.92 g of Compound F (where $R^1$ is dimethyltridecyl) hydrochloride salt for an isolated yield of 43%.

$^1$H NMR (400 MHz, $CD_3OD$): δ 7.12 (d, 2H), 6.75 (d, 2H), 5.18 (d, 1H), 4.97 (d, 1H), 1.19 (d, 3H), 0.89 (t, 3H), 0.86 (d, 6H).

Mass spectrum (FAB) m/z $(M+Li)^+$: 1058.

Part B. Preparation of Compound G

A solution of Compound F as the hydrochloride salt (41.4 g, 0.038 mol), ethanolamine hydrochloride (100 g, 1.0 mol), and 4.0M hydrochloric acid in 1,4-dioxane (11.4 ml, 0.046 mol) in anhydrous dimethylsulfoxide (200 ml) was stirred at ambient temperature under a nitrogen atmosphere for a period of 66 hours. HPLC analysis (41% acetonitrile/water/0.1% trifluoroacetic acid) showed 6% unreacted Compound F ($t_R$=7.9 min) and 56% Compound G ($t_R$=4.2 min). The reaction mixture was diluted to 1 liter with water and filtered through a bed of filter aid. Pump-injection of the filtrate onto a preparative C18 HPLC column was followed by elution with 5–15% acetonitrile/water/0.1% acetic acid in 5% step gradients. The product-containing fractions (40% acetonitrile/water/0.1% trifluoroacetic acid, $t_R$=4.2 min) were combined and diluted 10% with water. Compound G was isolated by C18 solid-phase extraction eluting with methanol. Removal of the methanol in vacuo provided a syrup which was dissolved in 50% $CH_3CN$/water and lyophilized to give 18.1 g of Compound G as a mixture of hydrochloride and acetate salts suitable for use in the subsequent deacylation step. HPLC purity>80%. Rechromatography of a portion of the mixed salt followed by anion exchange to the dihydrochloride provided Compound G as the dihydrochloride salt. HPLC purity>99%.

$^1$NMR (400 MHz, $CD_3OD$): δ 7.12 (d, 2H), 6.77 (d, 2H), 5.18 (d, 1H), 3.14 (t, 2H), 3.09 (t, 2H).

Anal. ($C_{52}H_{89}Cl_2N_9O_{16}$) C, H, N, Cl. FRMS (FAB) m/z (M+1) Calculated for $C_{52}H_{88}N_9O_{16}$ 1094.6348 Found 1094.6338.

Part C. Deacylation of Compound G to Give Triamine H

Compound G was enzymatically deacylated as follows:
i. Preparation of *C. acidovorans* cells To establish a seed culture of *C. acidovorans* ATCC 53942, a loopful of cells from an LB agar slant of the organism was used to inoculate 50 mL of Lauria-Bertani (LB) medium in a 250-mL unbaffled Erlenmeyer flask. The flask was incubated at 25° C. with agitation at 220 rpm for about 18 hours and 0.1 mL of this culture was used to inoculate each of three 250-mL Erlenmeyer flasks containing 50 mL of LB medium. After incubating under the same conditions for 18 hours, 20 mL of the grown cells were used to inoculate 15 liters of LB medium in each of six 23-liter fermentors. The fermentors were operated at 30° C. with agitation at 400 rpm and aeration at 7.4 L/min for 18 hours. Cultures from three fermentors were combined, washed and concentrated to 11 liters in 50 mM potassium phosphate buffer, pH 7.5 using a hollow fiber ultrafiltration system.

ii. Deacylation of Compound G

Deacylation was set up in two 15-liter Microferm fermentors (New Brunswick Scientific). In one vessel (A), 10 g of Compound G dissolved in 250 mL of distilled water was added to 5 liters of the washed and buffered *C. acidovorans* cells while in the second vessel (B), 8.2 g of Compound G dissolved in 200 mL of distilled water was added to 4 liters of the cells. Addition of Compound G to each vessel was accomplished with a pipette over a 5-minute period. To reduce foaming, about 2 mL and 1.5 mL of P2000 were added to vessels A and B respectively. Each fermentor was operated with stirring at 100 rpm, aeration at 1.5 L/min and temperature at 37° C for the first 2.5 hours and 30° C. for the last 21.5 hours. After 24 hours, HPLC analyses indicated that deacylation was 100% complete in each vessel. The contents of both vessels were combined and the cells were removed by hollow fiber filtration. HPLC analysis confirmed that the filtrate contained Compound H, the nucleus of Compound G.

iii. Isolation of Compound H

The deacylation broth from the procedure above was processed by loading 17 L broth onto 4×120 g resin columns (BioRad AG50W-X8, H+ form). The columns were each washed with 1 L of water to pH=7.0 prior to loading the phosphate-buffered broth. Each loading was followed by 1 L water wash and compound H was then eluted with 0.15N $NH_4OH$. The product-containing fractions (approximately 2 L) were combined and lyophilized to give 10.3 g of crude Compound H (free amine). This was then slurried in 100 mL of water, cooled to 0° C. and 100 mL of 2% $CF_3COOH/H_2O$ was added (5 eq, pH=2). This was then loaded onto a 50 g RP-$C_{18}$ plug (rinsing with 0.1% aqueous trifluoroacetic acid). Lyophilization then gave 16.2 g of Compound H as the tri-TFA salt (~70% pure). A small portion was further purified on an Rx-$C_{18}$ column (21.2 mm×25 cm) using 5% $CH_3CN/H_2O$ (0.5% $CF_3COOH$). Elution at a flow rate of 10 ml/min was monitored by UV at 220 and 277 nm. The product-containing fractions, as determined by analytical C18-HPLC (4.6 mm×25 cm, 3.5% $CH_3CN/H_2O$ (0.1% $CF_3COOH$) at 1.5 ml/min, $t_R$=4.9 min) were combined and lyophilized to give >98% pure Compound H.

$^1$H NMR (500 MHz, $CD_3OD$): δ 7.13 (d, J=8.4 Hz, 2H), 6.75 (d, J=8.7 Hz, 2H), 5.24 (d, J=3.2 Hz, 1H), 5.01 (d, J=2.7 Hz, 1H), 4.42 (dd, J=5.5 and 11.2 Hz, 1H), 4.38 (d, J=7.8 Hz, 1H), 3.98 (dd, 3.1 and 11.1 Hz, 1H), 3.15 (m, 2H), 3.05 (t, J=7.3 Hz, 2H), 2.43(dd, J=6.9 and 13.0 Hz, 1H), 1.26 (d, J=6.2 Hz, 3H).

ESI-MS (M+H)$^+$=857.6 iv. Preparation of Compound I from Compound H

Step a.

To a stirred solution of Compound H (16.0 g [~70% pure], 0.0094 mol) in anhydrous dimethylformamide (75 ML) was added triethylamine (9.3 mL, 0.067 mol), followed by benzyl-4-nitrophenyl carbonate (5.11 g, 0.019 mol), and this was stirred for 20 minutes. HPLC indicated incomplete formation of Compound J (analytical C18-HPLC:30% acetonitrile/water/0.1% trifluoroacetic acid, $t_R$=3.7 min). Additional carbonate (1.46 g, 0.005 mol) was added and HPLC indicated mainly Compound J as product. The pentaflourophenyl 6-n-heptyloxy-2-napthoate (6.65 g, 0.015 mol) was then added and stirred for 18 hours. HPLC indicated consumption of Compound J and formation of acylated product, Compound K. The reaction was diluted with water (75 mL) and loaded onto a RP C18 flash column (50 g) packed in 30% $CH_3CN/H_2O$; rinsed with 6×50 mL of 50% $CH_3CN/H_2O$; and lastly 10×50 mL 100% methanol. The product-containing methanol fractions were combined and concentrated to give 11.1 g of crude Compound K (80% pure). A small portion of Compound K was further purified on Zorbax Rx-C18 (21.2×250 mm) eluting with 70% $CH_3CN/H_2O$ at a flow rate of 10 mL/min. The product-containing fractions, as determined by HPLC (75% A/B, $t_R$=3.1 min), were combined and lyophilized to give >98% pure Compound K.

$^1$H NMR (CD$_3$OD): δ 8.32 (s, 1H), 7.85 (d, J=7.6 Hz, 1H), 7.74 (d, J=8.9 Hz, 1H), 7.66 (d, J=8.7 Hz, 1H), 7.10–7.30 (m, 14H), 6.75 (d, J=8.5 Hz, 2H), 5.29 (s, 1H), 4.99 (m, 2H), 4.93 (s, 4H), 3.96 (dd, J=3.1 and 11.1 Hz, 1H), 3.61 (m, 1H), 3.52 (m, 1H), 3.40 (m, 1H), 2.43 (dd, J=6.9 and 13.0 Hz, 1H), 1.84 (m, 2H), 1.22 (d, J=6.1 Hz, 3H), 0.92 (t, J=6.9 Hz, 3H).

ESI-MS (M+TFA)$^-$=1505

Step b.

To a stirred suspension of Compound K (11.0 g [80% pure], 0.006 mol) in CH$_3$OH (200 mL) and CH$_3$COOH (20 mL) was added 5.5 g 10% Pd/C. This was then subjected to an atmosphere of hydrogen (balloon pressure) and allowed to stir for 3 hours. HPLC indicated complete deprotection and catalyst was filtered through a pad of diatomaceous earth, rinsing with CH$_3$OH, and concentration gave crude Compound I. This was then dissolved in water (150 mL) and loaded onto Delta Prep C18 for purification. A step-gradient chromatography from 10–30% acetonitrile/water/0.1% acetic acid was used and lyophilization of the appropriate fractions as determined by HPLC (35% acetonitrile/water/ 0.1% trifluoroacetic acid, $t_R$=4.7 min) gave 6.2 g of Compound I as the di-acetate salt. This was then dissolved in water (200 mL) and applied to a BioRad AG2-X8, Cl$^-$ resin column (70 g); elution with H$_2$O and subsequent lyophilization gave 5.8 g of Compound I as the dihydrochloride salt.

$^1$H NMR (CD$_3$OD): δ 8.36 (s, 1H), 7.80–7.90 (m, 3H), 7.28 (d, J=1.8 Hz, 1H), 7.21 (dd, J=2.2 and 9.0 Hz, 1H), 7.13 (d, J=8.5 Hz, 2H), 6.76 (d, J=8.5 Hz, 2H), 5.29 (s(br), 1H), 5.03 (d, J=3.0 Hz, 1H), 4.94 (d, J=6.6 Hz, 2H), 4.76 (dd, J=4.7 and 12.9 Hz, 1H), 4.13 (m, 3H), 3.87 (t, J=6.8 Hz, 2H), 3.18 (m, 2H), 3.10 (t, J=5.5 Hz, 2H), 2.45 (dd, J=7.0 and 12.7 Hz, 1H), 1.53 (m, 2H), 1.22 (d, J=6.2 Hz, 3H), 0.92 (t, J=6.9 Hz, 3H).

Anal. (C$_{54}$H$_{79}$Cl$_2$N$_9$O$_{17}$) C, H, N, Cl. ESI-MS (M+H)$^+$ =1094.6

EXAMPLE 2

Part A. Deacylation of Pneumocandin B$_O$

The preparation of the deacylating enzyme is first described. A loopful of *Comamonas acidovorans* ATCC 53942 is inoculated into 50 milliliters of Luria Bertani medium of the following composition: per liter Bacto-Trypton, 10 g; Bacto-Yeast Extract, 5 g and sodium chloride 10 g and solidified with 2 percent agar and incubating for 24 hours with shaking to obtain a seed culture. Cells for the deacylation are then grown by diluting a 50 milliliter portion of seed culture 1:500 into fresh Luria-Bertani medium and incubating at 25° C. with shaking for 16 hours. Cells are then harvested by centrifugation, washed by resuspending in 1 percent sodium chloride and centrifuged and then resuspended in potassium phosphate buffer at pH 6.5.

A solution of pneumocandin B$_O$ (Compound E) in dimethylsulfoxide is then added to a stirred suspension of the cells of *C. acidovorans* thus obtained and the mixture maintained at 37° C. for 18 hours to obtain the deacylated product, Compound L, which is recovered in the supernatant after centrifugation.

Compound L may be isolated by adsorbing the supernatant on HP-20 resin with water, eluting with methanol and concentrating the eluates. The eluates are combined, diluted with water, charged to a preparative HPLC system equipped with a Whatman Partisil 10 SCX column and then eluted with 0.01M potassium phosphate (pH=6) buffer and monitored via UV at 210 nm. Cuts rich in the deacylated product were combined and the resulting mixture absorbed and eluted from HP-20 resin with methanol to remove buffer salts and to obtain Compound L with a molecular weight of 826.

Part B. Reacylation of Compound L to Give Compound M

Pentafluorphenyl 6-n-heptyloxy-2-naphthoate is prepared as follows. To a suspension of 6-n-heptyloxy-2-naphthoic acid (10.5 mmol) and dicyclohexylcarbodiimide (10.5 mmol) in ethyl acetate at 0° C. is added pentafluorophenol (11.5 mmol). The mixture is stirred at 25° C. for a period of 18 h. Any precipitate is removed by filtration. The filtrate is washed twice with water and brine and dried with magnesium sulfate. Removal of the ethyl acetate in vacuo gives the desired pentafluorophenyl 6-n-heptyloxy-2-naphthoate.

Pentafluorophenyl 6-n-heptyloxy-2-naphthoate (1.1 mmol) prepared as above is added to a solution of Compound L from Part A (1.0 mmol) in anhydrous N,N-dimethylformamide. The resulting solution is stirred at room temperature for a period of 12 to 24 h. The mixture is subsequently diluted with water. C18-Flash chromatography of the mixture eluting with 30–100% CH$_3$CN/H$_2$O in 10% step gradients followed by lyophilization of the product-containing fractions as determined by analytical HPLC (Zorbax RX-C18, UV detection at 210 nm) gives the desired Compound M with a molecular weight of 1095.2.

Part C. Reduction of Compound M to Give Compound N

A reaction vessel is outfitted with an addition funnel charged with 3–4 angstrom molecular sieves and a reflux condenser above the addition funnel. Within the reaction vessel, Compound M is suspended in dry tetrahydrofuran and heated to reflux under a nitrogen atmosphere. The mixture is refluxed for 12–24 hours, then cooled to 0° C. Borane-methylsulfide complex (10–20 equivalents) is added dropwise over 1–2 hours. The mixture is stirred at 0° C. for 2–5 hours and then carefully quenched with 2N hydrochloric acid. Stirring is continued for 1 hour after the final addition of hydrochloric acid. The mixture is concentrated to 40–50 percent of the original volume and then diluted with 6–7 volumes of distilled water. Purification by preparative reverse phase HPLC (DeltaPak C18, acetonitrile/water/0.1% acetic acid, UV detection at 210 nm) and subsequent lyophilization of the appropriate fractions, as determined by analytical HPLC, gives the desired compound. The hydrochloride salt is prepared by passage of an aqueous solution of the residue through an anion exchange column (BioRad AG2-X8, Cl⁻ resin) to give the desired Compound N with a molecular weight of 1117.6.

Part D. Aminoethyletherification of Compound N to Compound I

To a solution of the cyclohexapeptidyl propanolamine compound (N) (0.2 mmol) in DMSO (8 mL) containing 2-aminoethanol as the hydrochloride salt (20 mmol, 100 eq based on the cyclohexapeptide propanolamine) is added 4M HCl in dioxane (0.4 mmol) and the mixture is stirred at room temperature for two to seven days. The progress of the reaction may be monitored by HPLC using a 0.5 cm X 25 cm analytical Zorbax C18 column eluted with a mixture of acetonitrile and water containing 0.1% trifluoroacetic acid (typically the solvent was from 10–50% acetonitrile). When the reaction is judged to be complete, the reaction mixture is diluted with five to ten volumes of water and the resulting mixture applied to a reverse phase flash silica gel column using Lichroprep C18 (particle size 40–63 microns). The mixture is then eluted initially with 5%–15% acetonitrile in water to remove the excess DMSO and 2-aminoethanol hydrochloride, then with 10–50% acetonitrile in water to elute the product. Fractions containing the desired product are combined, concentrated and lyophilized to afford the product. Subsequent exchange for chloride ion may be accomplished by dissolving the residue in water and passing through a BioRad AG2-X8, Cl⁻ resin column to give the desired Compound I as the dihydrochloride with a molecular weight of 1197.2.

---

---

What is claimed is:

1. A compound of the formula

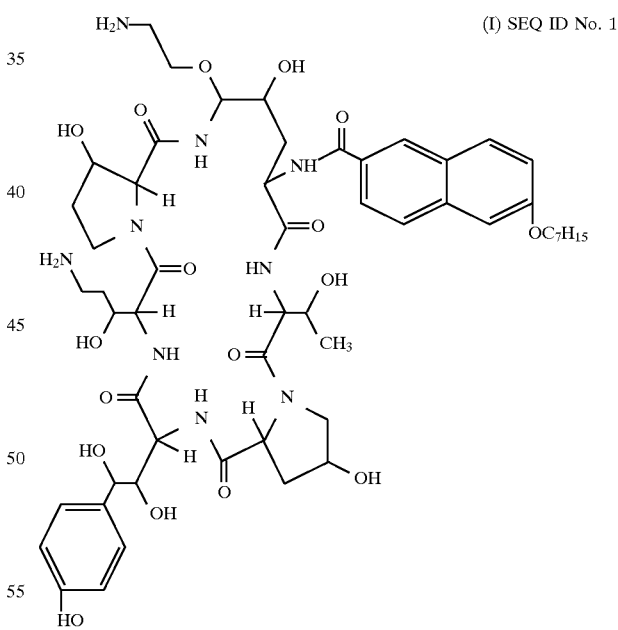

(I) SEQ ID No. 1 or an acid addition salt thereof.

2. A compound as defined in claim 1 where the acid addition salt is selected from the group consisting of acetate, trifluoroacetate, chloride, bromide, tartrate, succinate, glutamate, sulfate, phosphate and pamoate.

3. A compound defined in claim 2 wherein the acid addition salt is trifluoroacetate or hydrochloride.

4. A pharmaceutical composition comprised of a compound as defined in claim 1 in combination with a pharmaceutically acceptable carrier therefor.

5. A pharmaceutical composition as claimed in claim 4 where the acid addition salt is selected from the group consisting of acetate, trifluoroacetate, chloride, bromide, tartrate, succinate, glutamate, sulfate, phosphate and pamoate.

6. A pharmaceutical composition as claimed in claim 5 wherein the acid addition salt is trifluoroacetate or hydrochloride.

7. A method for treating fungal infections in a patient in need of such treatment, comprising administering to said patient an effective amount of the compound as defined in claim 1.

8. A method for treating fungal infections in a patient in need of such treatment, comprising administering to said patient an effective amount of a compound as defined in claim 2.

9. A method for treating fungal infections in a patient in need of such treatment, comprising administering to said patient an effective amount of a compound as defined in claim 3.

10. A method for treating an infection caused by *Candida sp.* in a patient which comprises administering to said patient an effective amount of a compound as defined in claim 1.

11. A method for treating an infection caused by *Candida sp.* in a patient which comprises administering to said patient an effective amount of a compound as defined in claim 2.

12. A method for treating an infection caused by *Candida sp.* in a patient which comprises administering to said patient an effective amount of a compound as defined in claim 3.

13. A method for treating an infection caused by Aspergillus sp. in a patient which comprises administering to said patient an effective amount of a compound as defined in claim 1.

14. A method for treating an infection caused by *Aspergillus sp.* in a patient which comprises administering to said patient an effective amount of a compound as defined in claim 2.

15. A method for treating an infection caused by *Aspergillus sp.* in a patient which comprises administering to said patient an effective amount of a compound as defined in claim 3.

16. A method for treating or an infection or condition caused by *Pneumocystis carinii* in a patient in need of such treatment or which comprises administering to said patient a preventative or therapeutic amount of the compound of claim 1.

17. A method for treating or an infection or condition caused by *Pneumocystis carinii* in a patient in need of such treatment or which comprises administering to said patient a preventative or therapeutic amount of the compound of claim 2.

18. A method for treating or an infection or condition caused by *Pneumocystis carinii* in a patient in need of such treatment or which comprises administering to said patient a preventative or therapeutic amount of the compound of claim 3.

* * * * *